(12) United States Patent
Loscutoff et al.

(10) Patent No.: US 11,908,558 B2
(45) Date of Patent: Feb. 20, 2024

(54) PROSPECTIVE MEDICATION FILLINGS MANAGEMENT

(71) Applicant: Clover Health, Jersey City, NJ (US)

(72) Inventors: Peter Vladimir Loscutoff, Berkeley, CA (US); Christopher James Lauinger, Golden, CO (US)

(73) Assignee: Clover Health, Jersey City, NJ (US)

( * ) Notice: Subject to any disclaimer, the term of this patent is extended or adjusted under 35 U.S.C. 154(b) by 209 days.

(21) Appl. No.: 16/140,414

(22) Filed: Sep. 24, 2018

(65) Prior Publication Data
US 2020/0098456 A1  Mar. 26, 2020

(51) Int. Cl.
| | | |
|---|---|---|
| *G16H 20/10* | (2018.01) | |
| *G06F 9/54* | (2006.01) | |
| *G16H 10/60* | (2018.01) | |
| *G06N 20/00* | (2019.01) | |
| *G06N 7/01* | (2023.01) | |
| *G16H 20/00* | (2018.01) | |
| *G06N 20/10* | (2019.01) | |
| *G06N 20/20* | (2019.01) | |
| *G16H 40/20* | (2018.01) | |
| *G16H 40/63* | (2018.01) | |
| *G16H 40/67* | (2018.01) | |
| *G06Q 10/109* | (2023.01) | |

(52) U.S. Cl.
CPC .............. *G16H 20/10* (2018.01); *G06F 9/542* (2013.01); *G06N 7/01* (2023.01); *G06N 20/00* (2019.01); *G06N 20/10* (2019.01); *G06N 20/20* (2019.01); *G06Q 10/109* (2013.01); *G16H 10/60* (2018.01); *G16H 20/00* (2018.01); *G16H 40/20* (2018.01); *G16H 40/63* (2018.01); *G16H 40/67* (2018.01)

(58) Field of Classification Search
CPC ........ G06F 9/542; G06N 7/005; G06N 20/00; G06N 20/10; G06N 20/20; G06N 7/01; G16H 10/60; G16H 20/00; G16H 20/10; G16H 40/20; G16H 40/63; G16H 40/67; G06Q 10/109
See application file for complete search history.

(56) References Cited

U.S. PATENT DOCUMENTS

| | | | |
|---|---|---|---|
| 8,786,650 B1 * | 7/2014 | Eller | B41J 2/435 347/224 |
| 9,773,094 B1 * | 9/2017 | Balagere | G06Q 10/06395 |
| 9,894,498 B2 * | 2/2018 | Van Snellenberg | H04W 4/00 |

(Continued)

OTHER PUBLICATIONS

PCT Search Report and Written Opinion dated Dec. 18, 2019, for PCT Application No. PCT/US19/52563, 8 pages.

*Primary Examiner* — Jonathan Ng
*Assistant Examiner* — Hunter J Rasnic
(74) *Attorney, Agent, or Firm* — Lee & Hayes, P.C.

(57) ABSTRACT

Systems and methods for medication fillings management are disclosed. For example, user information and/or refill schedules associated with users may be utilized to predict which users are likely to miss a medication refill. The presently disclosed systems and methods may determine health indicators associated with users and, by utilizing one or more machine learning techniques, determine which health indicators, alone or in combination, are associated with users prone to missing refills. As such, the system may predict users that are likely to miss a refill and may generate preemptive, targeted refill reminders in order to prevent the missed refill before it occurs.

20 Claims, 6 Drawing Sheets

(56) References Cited

U.S. PATENT DOCUMENTS

| | | | |
|---|---|---|---|
| 2005/0060200 A1* | 3/2005 | Kobylevsky | G06Q 30/06 705/2 |
| 2006/0122866 A1* | 6/2006 | Hadl | G16H 20/10 705/2 |
| 2007/0143137 A1* | 6/2007 | Ross | G16H 10/20 705/2 |
| 2007/0168228 A1* | 7/2007 | Lawless | G06Q 40/08 600/300 |
| 2008/0059242 A1* | 3/2008 | Stanford | G16H 10/60 707/999.107 |
| 2008/0126130 A1* | 5/2008 | Miller | G16H 20/10 705/3 |
| 2008/0287746 A1* | 11/2008 | Reisman | G16H 40/63 600/300 |
| 2008/0312966 A1* | 12/2008 | Meshginpoosh | G16H 10/65 705/3 |
| 2009/0281835 A1* | 11/2009 | Patwardhan | G06Q 30/0267 705/3 |
| 2010/0185456 A1* | 7/2010 | Kansal | G16H 50/20 705/2 |
| 2010/0314282 A1* | 12/2010 | Bowers | A61J 7/04 206/534 |
| 2011/0082705 A1* | 4/2011 | Kobylevsky | G16H 80/00 705/2 |
| 2011/0215933 A1* | 9/2011 | Darling, IV | G06Q 10/109 340/573.1 |
| 2012/0065987 A1* | 3/2012 | Farooq | G16H 50/70 705/2 |
| 2013/0173277 A1* | 7/2013 | Eller | G16H 40/67 705/2 |
| 2014/0156298 A1* | 6/2014 | Crawford | G16H 10/60 705/2 |
| 2014/0262690 A1* | 9/2014 | Henderson | G06Q 50/22 198/602 |
| 2015/0032465 A1* | 1/2015 | Sundar | G16H 20/10 705/2 |
| 2015/0058034 A1* | 2/2015 | Ayshford | G06F 19/3456 705/2 |
| 2015/0058035 A1* | 2/2015 | Ayshford | G06F 19/3456 705/2 |
| 2016/0012194 A1* | 1/2016 | Prakash | G16H 40/40 705/2 |
| 2017/0054669 A1* | 2/2017 | Lewis | H04L 51/224 |
| 2017/0098037 A1* | 4/2017 | Agassi | G16H 10/60 |
| 2018/0075212 A1* | 3/2018 | Kubey | G16H 40/20 |

* cited by examiner

500

Receiving data from additional users including reminders to refill reminders sent to devices associated with the additional users and indications that the additional users have refilled the medications
502

Determining, based at least in part on machine learning techniques, combinations of indicators that are associated with probabilities exceeding the first probability threshold, the probabilities indicating that the additional users will miss refills
504

Determine that a refill of a medication prescribed to a user will occur within a threshold period of time
506

Predict, based at least in part on the combinations of indicators and machine learning techniques, that the user will miss refilling the medication
508

Generate a reminder to refill the medication
510

FIG. 5

PROSPECTIVE MEDICATION FILLINGS MANAGEMENT

BACKGROUND

Patients consuming prescription medications on a regular basis may sometimes fail to obtain refills for a variety of reasons. When a patient fails to obtain a refill, there may be an increased likelihood for health-related complications, leading to increased medical care expenses for both the individual and their insurance provider. Described herein are improvements in technology and solutions to technical problems that can be used to, among other things, assist with prescription refills.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference numbers in different figures indicates similar or identical items. The systems depicted in the accompanying figures are not to scale and components within the figures may be depicted not to scale with each other.

FIGS. 4-6 illustrate various flow diagrams of example processes for prospective medication fillings management.

DETAILED DESCRIPTION

Figure 1:
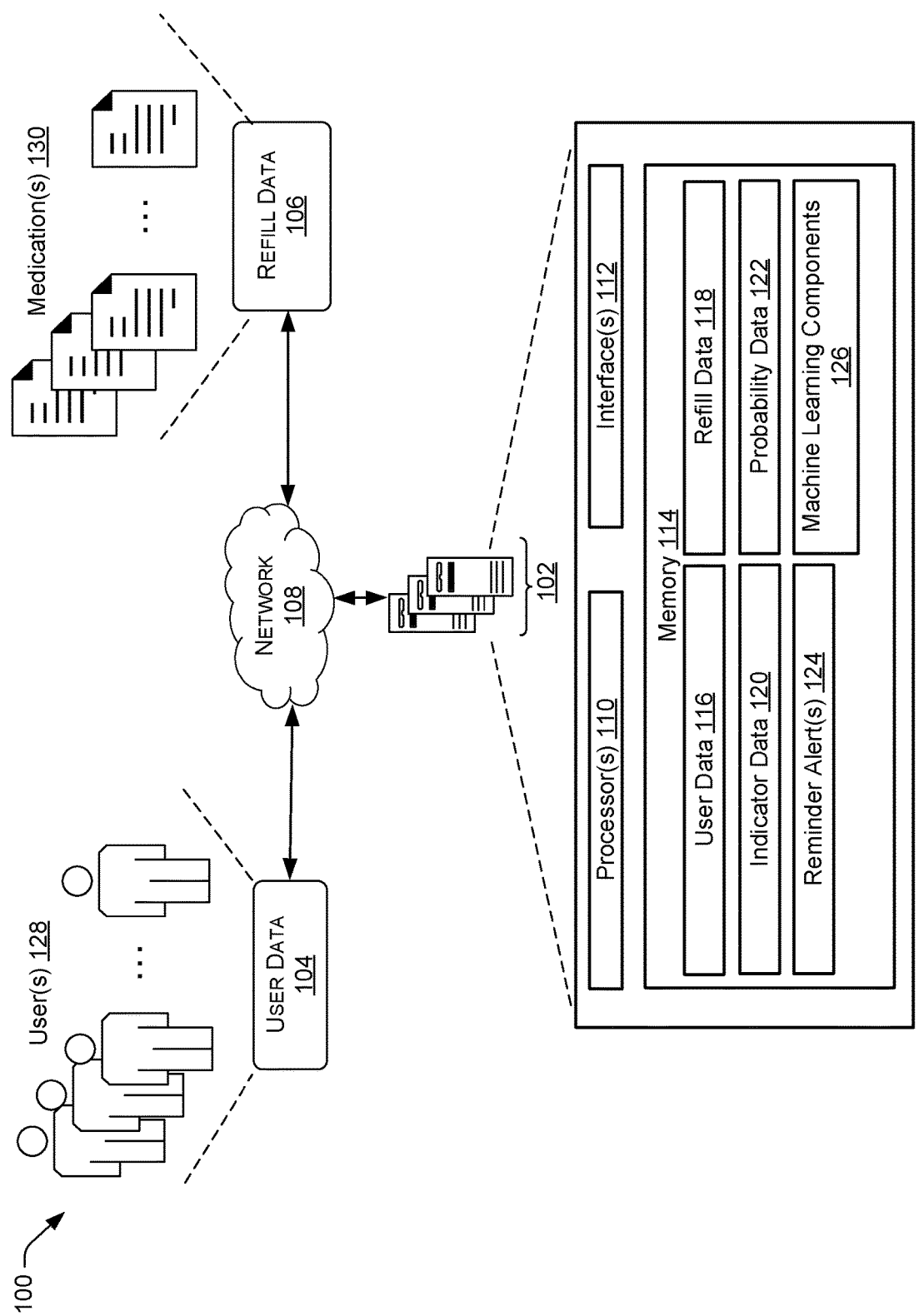
FIG. 1 illustrates a schematic diagram of an example environment for prospective medication fillings management.

Systems and methods for prospective medication fillings management are described herein. For example, certain users that are prescribed medications may be prone to missing refills for a variety of reasons. In some instances, indicators such as social factors, medical history, and other user information may be associated with a higher likelihood that a user will miss a refill. With conventional systems, an alert can be sent, such as from a pharmacy, to a system after a user has already missed a refill. However, receiving an alert after a missed refill does not allow the system to take active steps to prevent the missed refill from occurring and avoid the negative effects, such as adverse health effects, higher costs of healthcare, etc. In addition, conventionally, the alert is generated after a certain period of time has lapsed to ensure accuracy (e.g., if the alert is sent too soon, the user may still refill). Thus, steps cannot be taken to remind the user ahead of time or in a timely manner after the refill is missed. As such, the need arises to implement systems and methods for prospective medication fillings management that will allow a system to accurately determine indicators associated with high-risk users in order to predict which users are likely to miss a refill. In this way, the system may take preemptive, targeted measures to prevent the missed refill in a timely manner.

The present invention is directed to systems and methods that employ predictive techniques and machine learning models to accurately predict that a user will miss a refill and take proactive steps to prevent the missed refill from occurring. For example, the system may access, or receive, user information associated with one or more users that are prescribed one or more medications. The user information may include user data such as demographic data, medical history, physical characteristics, prescription information including refill schedules, etc. that may be obtained from a user database, are provided by the user, and/or are accessed from one or more medical databases. The system may analyze the user information to identify one or more health indicators associated with users. For example, the system may determine a refill history of the user(s), social indicator(s) (e.g., low income or lives in a rural area), medical history indicator(s) (e.g., history of mental illness, alcoholism, etc.), and/or prescription indicator(s) (e.g., how many prescriptions are prescribed to the user) associated with the user(s). In addition, based at least in part on the user information, the system may also determine when a user is due for a refill of a prescription.

In examples, the system may utilize the one or more health indicators to determine that a probability the user will miss refilling the prescription exceeds a certain threshold. For example, the system may determine a refill history associated with the user to determine a probability that the user will miss refilling the prescription. The system may then determine if the probability exceeds (e.g., is above, for example) a predetermined threshold, indicating that the user is high-risk. For example, the system may determine if there is a 40% or higher probability that the user will miss his/her refill. If the probability exceeds the threshold, the system may activate one or more reminder mechanisms to deter the user from missing the refill. For example, the system may send a reminder to a user device associated with the user, contact a caregiver and/or care facility of the user, etc.

Additionally, the system may receive a refill indication that the user has interacted with the reminder and/or that the user has refilled the medication. For example, the system may receive an indication that the user has scheduled a refill via the reminder and/or a refill notification from a pharmacy that processed the refill. Based at least in part on the refill indication and the one or more health indicators, the system may determine if the reminder, type of reminder, and/or content of the reminder was effective in aiding the user in refilling the medication they were likely to miss.

In the examples described herein, the system may perform similar operations regarding multiple users. For example, the system may receive and/or access user information regarding a multitude of users. Utilizing the user information, the system may determine one or more health indicators of one or more of the users, determine probabilities that such users will miss a medication refill, generate reminders, receive refill indications, and determine an effectiveness of the reminders. From this information, the system may implement one or more machine learning techniques to determine which indicators, individually or in combination, are associated with users likely to miss a refill and/or responsive to reminders for refilling his/her medications. In addition, through the one or more machine learning techniques, the system may learn the type of reminder that is most effective among high-risk users.

Additionally, or alternatively, the systems and methods described herein may be configured to determine, based at least in part on the refill indications received, whether to generate and transmit future reminders to a user and/or what type of reminders are effective for a particular user. For example, the refill indicator can indicate that the user that received the refill reminder has not interacted with the reminder and/or has not refilled his/her medication. As such, the system may determine that the user should not receive future reminders. Alternatively, the refill indicator may indicate that the user has interacted with the reminder and/or has refilled his/her medication and should receive future reminders. In addition, the refill indicator may be compared with a certain threshold of effectiveness. For example, if the user has/has not interacted with a certain percentage of reminders, the user may or may not receive future reminders. In addition, the refill indicator(s) may indicate that the user has interacted with some reminders and not others. As such, the system may determine that a type of reminder is more effective for the user and may only transmit that type of reminder to the user in the future.

By using predictive learning techniques, the system may proactively target users who are prone to missing refills and ensure that effective reminders are sent that will ensure a user response. In this way, accessible user information can be utilized to increase refill compliance and reduce elevated health care costs associated with missed refills. In contrast to conventional techniques involving human decision-makers, the techniques described herein allow the system to make real-time and/or automated predictions and determinations regarding user refill behavior, whether a reminder should be sent, the type of reminder, etc. with improved speed and accuracy.

Additionally, the rules, algorithms, and various techniques described herein are designed to be implemented utilizing computerized components, as described herein, and could not be performed by human decision-makers while achieving the same results. In addition, the results achieved from the combination of steps performed and/or data points considered, allow the algorithms and machine learning techniques to constantly improve the functioning of the computerized components. For example, by more accurately predicting users at risk for missing a refill, based on a specific method and/or data points, the system may send out less reminders, reminders less frequently, etc. as a result of determining/predicting which users to target, the type of reminder to send, when to send the reminder, and/or the content of the reminder. More specifically, since the system can determine/predict characteristics of reminders with greater accuracy, to increase efficacy of the reminders, the computer may utilize less resources sending extraneous reminders. In addition, by refining the process using machine learning techniques and iterative algorithms, the computer may increase efficiency as more data points are collected.

Also, the user alerts, or reminders, described herein are time-sensitive in nature and configured to be transmitted to a user device in real-time for display on a user device via an interface, application program, etc. In this way, the reminders will cause the user device to display the reminder in a timely manner and increase the likelihood that the user will interact with the reminder and fulfill his/her refills.

The present disclosure provides an overall understanding of the principles of the structure, function, manufacture, and use of the systems and methods disclosed herein. One or more examples of the present disclosure are illustrated in the accompanying drawings. Those of ordinary skill in the art will understand that the systems and methods specifically described herein and illustrated in the accompanying drawings are non-limiting embodiments. The features illustrated or described in connection with one embodiment may be combined with the features of other embodiments, including as between systems and methods. Such modifications and variations are intended to be included within the scope of the appended claims.

Additional details are described below with reference to several example embodiments.

FIG. 1 illustrates a schematic diagram of an example environment 100 for prospective medication fillings management. The environment 100 may include, for example, a system 102 configured to receive user information including user data 104 and refill data 106 via a network 108. It should be understood that, while FIG. 1 depicts one system, the environment 100 may include any number of systems configured to operate independently and/or in combination and configured to communicate with each other via the network 108. It should also be understood that while the object is described as a "system," the object may be considered a device. The components of the system 102 will be described in detail below.

For example, the system 102 may include one or more processors 110, one or more network interfaces 112, and memory 114. The memory 114 may include one or more components, such as, for example, a user data component 116, a refill data component 118, an indicator data component 120, a probability data component 122, a reminder alert(s) component 124, and one or more machine learning components 130. At least some of the components of the memory 114 will be described below.

The user data component 116 may be configured to store and/or access data associated with the system 102. The data may be any data associated with the system 102. In examples, the data may be the user data 104. For example, the user data 104 may be data associated with multiple users 130 utilizing the system 102. In particular, the user data 104 may include data associated with at least some of the users 130 including, but not limited to, personal data, demographic data, health data, physical characteristic data, prescription medication data, social data, and/or any other data provided by the users 130 or able to be obtained from medical records associated with the users 130.

In examples, the user data 104 may be transmitted to the system 102 via the network 108 from one of the users 128 or a third-party system. In other examples, the user data 104 may be accessed from an external storage component, such as a database or cloud-based storage device, by the system 102. The user data 104 may be utilized by the system 102 to determine one or more health indicators associated with at least some of the users 130, as described herein.

The refill data component 118 may be configured to store and/or access additional data associated with the system 102. In examples, the additional data may be the refill data 106. For example, the refill data 106 may include data associated with one or more medications 130 prescribed to the users 130. In particular, the medications 130 may include maintenance medications (e.g., medications taken on a regular basis for a prolonged period of time) and/or any other medication requiring a refill. Note that the term refill may herein refer to a fill, and vice versa.

In examples, the refill data 106 may be transmitted to the system 102 via the network 108 and/or may be accessed from an external storage component, such as a database or cloud-based storage device, by the system 102. The refill data 106 may be utilized by the system 102 to determine information associated with a refill for each medication prescribed to at least some of the users 130. For example, the refill data 106 may include, but not be limited to, data associated with the medications 130 such as name, brand information, approved generics dosage, refill frequency, refill schedules, remaining refills, preferred pharmacy, and/or any other information pertinent to a prescription refill.

In examples, the indicator data component 120 may be configured to access the user data 104 of the user data component 116 to determine one or more health indicators associated with at least some of the users 130, such as a refill history, medical conditions, physical characteristics, social indicators, etc. For example, the indicator data component 120 may utilize the user data 104 to determine the refill history associated with the user. The refill history may indicate a frequency with which the user fulfills and/or misses refill requirements for his/her medications 130. In other examples, the indicator data component 120 may utilize the user data 104 to determine whether the medical history associated with the user includes any medical ailments or chronic illnesses. For example, the user data 104 may include medical history data for the user and the system may analyze the user data 104 to determine if the user has any medical conditions such as alcoholism, mental health afflictions, etc. that may indicate that the user may be at risk for missing a medication refill. Additionally, the indicator data component 120 may utilize the user data 104 to determine one or more physical characteristics associated with the user. For example, the medical history data may indicate one or more physical characteristics such as eye color, obesity, etc. Additionally, the indicator data component 120 may utilize the user data 104 to determine one or more social indicators such as a living situation (e.g., living at home, with a caretaker, in an assisted living facility, etc.), a marital status, access to transportation, etc.

In examples, the probability data component 122 may be configured to store probability threshold data associated with the system 102 and/or determine refill probabilities associated with the users 132. For example, the probability data component 122 may access the health indicators determined by the indicator data component 120 to determine a probability, or likelihood, that the user will miss a medication refill. As described herein, the health indicator(s) may indicate a refill history, social indicators, etc. associated with the user. As a specific example, based at least in part on the refill history indicating that the user has missed a certain percentage of his/her previous refills, the probability data component 122 may determine that the user is 50% more likely (e.g., has a 50% probability) to miss an upcoming refill.

In addition, the probability data component 122 may utilize one or more machine learning components 130, as described herein, to determine the probability threshold data associated with a user or group of users based at least in part on historical data. For example, the probability data component 122 may utilize one or more machine learning components 130, described in greater detail below, to determine that users who do not own a motor vehicle are 10% more likely to miss a refill. This probability data, combined with the probability data determined based at least in part on the one or more health indicators, may be utilized to determine an overall probability that the user will miss an upcoming refill. In the examples described herein, one or more predictive algorithms and/or application programming interfaces (APIs) may be included and may be utilized by the probability data component 122 to calculate the probability data associated with the users 130.

Additionally, the probability data component 122 may store probability thresholds that have been predetermined by the system 102 or pre-programmed into the system 102. For example, the system 102 may have previously determined a threshold that, if exceeded, causes the system to generate a user alert. Alternatively, or in addition to, the system 102 may have been preprogrammed with probability thresholds based at least in part on data, observations, etc. The probability data component 122 may compare the determined probability with the stored probability to determine whether to generate a reminder, or user alert, to send to the user. For example, the system 102 may have determined that it is worthwhile to generate a reminder if the probability threshold exceeds a 40% likelihood that the user will miss a refill.

In examples, the reminder alert(s) component 124 may be configured to generate and transmit reminder alert(s), such as refill reminders to the users 130, and receive user responses associated with the reminder alert(s). For example, the reminder alert(s) component 124 may receive a signal from the probability data component 122 to cause the reminder alert(s) component 124 to generate a refill reminder for a user. As described above, when the probability data component 122 determines that a determined probability exceeds a probability threshold, the probability data component 122 may transmit a signal to the reminder alert(s) component 124 to cause the reminder alert(s) component 124 to generate a refill reminder. The refill reminder may include, but not be limited to, a notification for display on a device associated with the user, a communication to caregiver or facility associated with the user (e.g., as indicated by the user data 104), etc. Additionally, in examples, the notification or communication may include a service and/or service suggestion that may assist the user in scheduling a refill, such as a link to a pharmacy website, a link to or schedule suggestion for a means of transportation, etc.

Additionally, the reminder alert(s) may be configured to cause an application residing on the user device to be activated and display the alert to the user. For example, the reminder alert(s) may cause a device application to activate and display the refill reminder including reminder information and/or generate an interactive user interface including the reminder information, selectable elements, interactive links, etc. In addition, due to the need to adhere to a prescribed refill schedule, the reminder alert(s) may be time-sensitive in nature. For example, the refill reminders may be configured to be transmitted to the user device in real-time as the user's likelihood to miss a refill is determined and/or within a certain time period before the refill is due. For example, the reminder alert(s) component 124 may determine, through predetermined parameters or machine learning techniques, that the refill reminder must be transmitted during a certain time of day and/or at least a certain amount of days/hours/minutes before a refill is due in order to increase the effectiveness of the alert.

In examples, the reminder alert(s) component 124 may utilize one or more of the user data 104, the indicator data, and/or the machine learning components 126 to determine the most effective type of reminder for user(s) and/or when and how it is transmitted. For example, the reminder alert(s) component 124 may access the user data 104, via the user data component 116, the one or more health indicators, via the indicator data component 120, and/or the probability data, via the probability data component 122, to determine one or more aspects of the refill reminder. For example, the user data 104 may indicate that the user does not have a mobile device and/or resides in a caretaker facility. In this instance, the reminder alert(s) component 124 may determine that the refill reminder should include a communication directly to the caretaker facility. In another example, the one or more health indicators may indicate that the user resides in a rural area that is not in close proximity to a brick-and-mortar pharmacy location. In this instance, the reminder alert(s) component 124 may determine that the refill reminder should include a link to an online medication provider. In yet another example, the one or more machine learning components 126 may provide data indicating that, based at least in part on historical data, the user is more likely to respond to an email refill reminder rather than a mobile refill reminder. In this instance, the reminder alert(s) component 124 may determine that the refill reminder should only include an email communication to the user.

In examples, the reminder alert(s) component 124 may be configured to receive, via the network 108, and/or store data relating to, any user interaction with the transmitted refill reminders. For example, the reminder alert(s) component 124 may be configured to receive an indication that at least one of a user interaction with a refill reminder and/or a lack of interaction with the refill reminder. In addition, the indication may further include the type of user interaction received, such as a selection, a dismissal, etc. associated with the type and/or content of the refill reminder. The one or more indications may be stored, either locally or remotely, within a database for access by the system 102.

Further, the memory 114 may store one or more machine learning components 130 configured to train, or create, one or more medication fillings management models. As described in more detail in FIG. 2, the machine learning component(s) 130 may receive, such as during a user onboarding process and/or set-up process, training data that is utilized to train, generate, or otherwise determine the medication fillings management models. For example, the machine learning component(s) 130 may execute one or more algorithms (e.g., decision trees, artificial neural networks, association rule learning, or any other machine learning algorithm) to train medication fillings management models that determine, based at least in part on various data, one or more health indicators, individually or in combination with each other, that indicate that a user will likely miss a medication refill, an effectiveness of transmitting a reminder communication, and/or an effectiveness associated with various aspects of the type of reminder such as content, time, date, and/or means of communicating the reminder.

Information from stored and/or accessible data may be extracted from one or more databases, such as for example the user data component 116, refill data component 118, indicator data component 120, probability data component 122, and/or reminder alert(s) component 124, and may be utilized to predict trends and behavior patterns. The predictive analytic techniques may be utilized to determine associations and/or relationships between explanatory variables and predicted variables from past occurrences and utilizing these variables to predict the unknown outcome. The predictive analytic techniques may include defining the outcome and data sets used to predict the outcome. Then, data may be collected and/or accessed to be used for analysis.

For example, the machine learning components 126 may access data from the indicator data component 120 and/or reminder alert(s) component 124 relating to a particular user. More specifically, the machine learning components 126 may access one or more health indicators associated with the user and/or the type of refill reminder transmitted and/or interaction received. From this information, the machine learning components 126 may utilize the medication fillings management model(s) to determine one or more health indicators, or a combination of one or more health indicators, associated with users that are more likely to miss a refill, respond to or ignore a refill reminder, and/or the type, content, delivery method, etc. associated with a refill reminder that the user has, or is likely to, respond to. Utilizing this information, the system 102 can identify those users at a higher risk of missing a refill and target effective reminders to prevent future missed refills. In addition, the system 102 may identify health indicators not commonly associated with high-risk users and/or health indicators that, when taken individually, do not indicate a high-risk user but, when taken in combination, identify that the user is, in fact, high-risk for missed refills.

As used herein, a processor, such as processor(s) 110, may include multiple processors and/or a processor having multiple cores. Further, the processors may comprise one or more cores of different types. For example, the processors may include application processor units, graphic processing units, and so forth. In one implementation, the processor may comprise a microcontroller and/or a microprocessor. The processor(s) 110 may include a graphics processing unit (GPU), a microprocessor, a digital signal processor or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, at least some of the processor(s) 110 may possess its own local memory, which also may store program components, program data, and/or one or more operating systems.

The memory 114 may include volatile and nonvolatile memory, removable and non-removable media implemented in any method or technology for storage of information, such as computer-readable instructions, data structures, program component, or other data. Such memory 114 includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device. The memory 114 may be implemented as computer-readable storage media ("CRSM"), which may be any available physical media accessible by the processor(s) 110 to execute instructions stored on the memory 114. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other tangible medium which can be used to store the desired information and which can be accessed by the processor(s).

Further, functional components may be stored in the respective memories, or the same functionality may alternatively be implemented in hardware, firmware, application specific integrated circuits, field programmable gate arrays, or as a system on a chip (SoC). In addition, while not illustrated, each respective memory, such as memory 114, discussed herein may include at least one operating system (OS) component that is configured to manage hardware resource devices such as the network interface(s), the I/O devices of the respective apparatuses, and so forth, and provide various services to applications or components executing on the processors. Such OS component may implement a variant of the FreeBSD operating system as promulgated by the FreeBSD Project; other UNIX or UNIX-like variants; a variation of the Linux operating system as promulgated by Linus Torvalds; the FireOS operating system from Amazon.com Inc. of Seattle, Washington, USA; the Windows operating system from Microsoft Corporation of Redmond, Washington, USA; LynxOS as promulgated by Lynx Software Technologies, Inc. of San Jose, California; Operating System Embedded (Enea OSE) as promulgated by ENEA AB of Sweden; and so forth.

The network interface(s) 112 may enable communications between the components and/or devices shown in environment 100 and/or with one or more other remote systems, as well as other networked devices. Such network interface(s) 112 may include one or more network interface controllers (NICs) or other types of transceiver devices to send and receive communications over the network 108.

For instance, at least some of the network interface(s) 112 may include a personal area network (PAN) component to enable communications over one or more short-range wireless communication channels. For instance, the PAN component may enable communications compliant with at least one of the following standards IEEE 802.15.4 (ZigBee), IEEE 802.15.1 (Bluetooth), IEEE 802.11 (WiFi), or any other PAN communication protocol. Furthermore, at least some of the network interface(s) 112, 134, and/or 146 may include a wide area network (WAN) component to enable communication over a wide area network.

Figure 2:
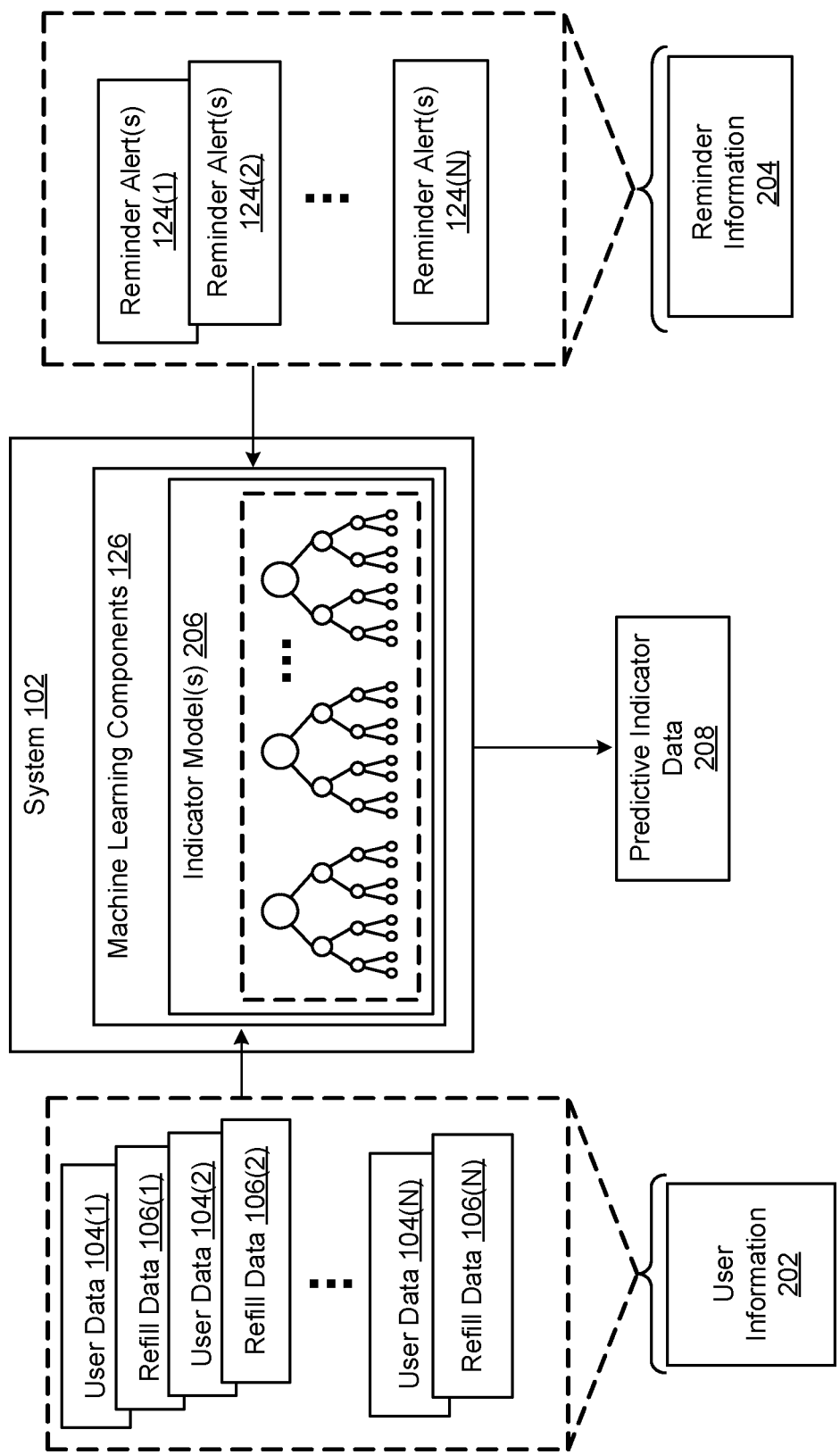
FIG. 2 illustrates an example of generating or training a model to identify one or more users at risk for missing a medication fill.

FIG. 2 illustrates an example of generating or training a model to identify one or more users at risk for missing a medication fill. For example, the one or more machine learning components 126 of computing device(s) 102, depicted and described in FIG. 1, may receive and/or determine user information 202. In examples, the user information 202 may include user data (e.g., user data 104(1), 104(2), ... 104(N)) and/or refill data (e.g., refill data 106(1), 106(2), ... 106 (N)). In addition, the one or more machine learning components 126, may receive and/or determine reminder information 204. In examples, the reminder information 204 may include reminder alert(s) (e.g., reminder alert(s) 124(1), reminder alert(s) 124 (2), ... reminder alert(s) 124 (N)) and/or refill data (e.g., refill data 106(1), 106(2), ... 106 (N)).

The user information 202 and/or reminder information 204 may be utilized by the one or more machine learning components 126 configured to execute one or more machine learning algorithms to train one or more indicator model(s) 206 to determine one or more health indicators associated with users. In addition, the one or more machine learning components 126 may be configured to identify which of the one or more health indicators, alone or in combination, are associated with users that are more likely to miss a refill, respond to or ignore a refill reminder, and/or the type, content, delivery method, etc. associated with a refill reminder that the user has, or is likely to, respond to. Although the indicator model(s) 206 is illustrated as a decision-tree trained model, the machine learning component(s) 126 may execute any type of supervised learning algorithms (e.g., nearest neighbor, Naïve Bayes, Neural Networks, unsupervised learning algorithms, semi-supervised learning algorithms, reinforcement learning algorithms, and so forth).

In examples, the user information 202 may include various user data 104 and refill data 106. For example, the user data 104 may include data associated with users such as personal data, demographic data, health data, physical characteristic data, prescription medication data, social data, and/or any other data provided by users or able to be obtained from medical records associated with the users. In other examples, the refill data 106 may include data associated with one or more medications prescribed to the users, such as refill schedules, frequency of refills, and/or dosage. Additionally, the reminder information 204 may include various data associated with the reminder alert(s) 124 that have been, or will be, generated and transmitted to the user. For example, the reminder alert(s) 124 may include data such as the type of reminder generated, the content of the reminder, and/or indications of user interactions with the reminder.

In examples, the machine learning component(s) 126 may train the indicator model(s) 206 based at least in part on user information 202 and refill information 204 received over time. For example, the user information 202 and refill information 204 may be associated with one or more persons, referred to herein as users. The indicator model(s) 206 may be trained to determine one or more health indicators associated with the users based at least in part on the user information 202. For example, the indicator model(s) 206 may be trained to determine a health indicator indicating a refill history associated with the user based at least in part on historical data. For example, the indicator model(s) 206 may determine, based at least in part on historical data associated with the user's refill, that the user misses 50% of his/her refills. The one or more indicators may be utilized by the indicator model(s) 206 to determine that the user is at a high-risk of missing a future refill and requires a reminder.

In other examples, the indicator model(s) 206 may be trained to determine one or more health indicators associated with users that have a pattern of missing refills. For example, the indicator model(s) 206 may utilize user information 202 and refill information 204 over time to learn that users associated with one or more health indicators have a high likelihood (e.g., over a certain threshold) of missing refills or a high occurrence of missing refills. As a specific example, the indicator model(s) 206 may be trained, over time, to determine that users who are divorced and/or live in rural areas have a high occurrence of missing refills, relative to other users not associated with those health indicators. As another specific example, the indicator model(s) 206 may be trained, over time, to determine that users who having certain physical characteristics, or ailments, may be more prone to missing refills relative to other users. The one or more health indicators, alone or in combination, associated with high-risk users may be determined and stored as predictive indicator data 208. In this way, when it is determined that another user is due for a refill, the system 102 may utilize the predictive indicator data 208 to predict if the user will miss his/her refill and send a preemptive reminder.

Additionally, in examples, the indicator model(s) 206 may be trained, over time, to determine the type, content, and means of communication that is most effective for users and/or associated with one or more health indicators. For example, the indicator model(s) 206, utilizing the user information 202 and refill information 204, may determine that users of a certain age are more likely to refill a medication if they receive a phone call reminder, in lieu of an email reminder. For example, based at least in part on historical user information 202 and refill information 204, the indicator model(s) 206 may determine that user data 104 indicating that a user is of a certain age is associated with the user responding to phone call reminders more often than email reminders. Alternatively, or in addition to, the indicator model(s) 206 may determine that a certain type of reminder is most effective among a current user group and may generate all future reminders accordingly. As such, the indicator model(s) 206 may be able to provide information to the system 102 to allow generation and transmission of intelligent, and targeted reminders to users, thereby increasing the likelihood that a user will interact with the reminder and/or resulting in the user refilling his/her medication.

Figure 3:
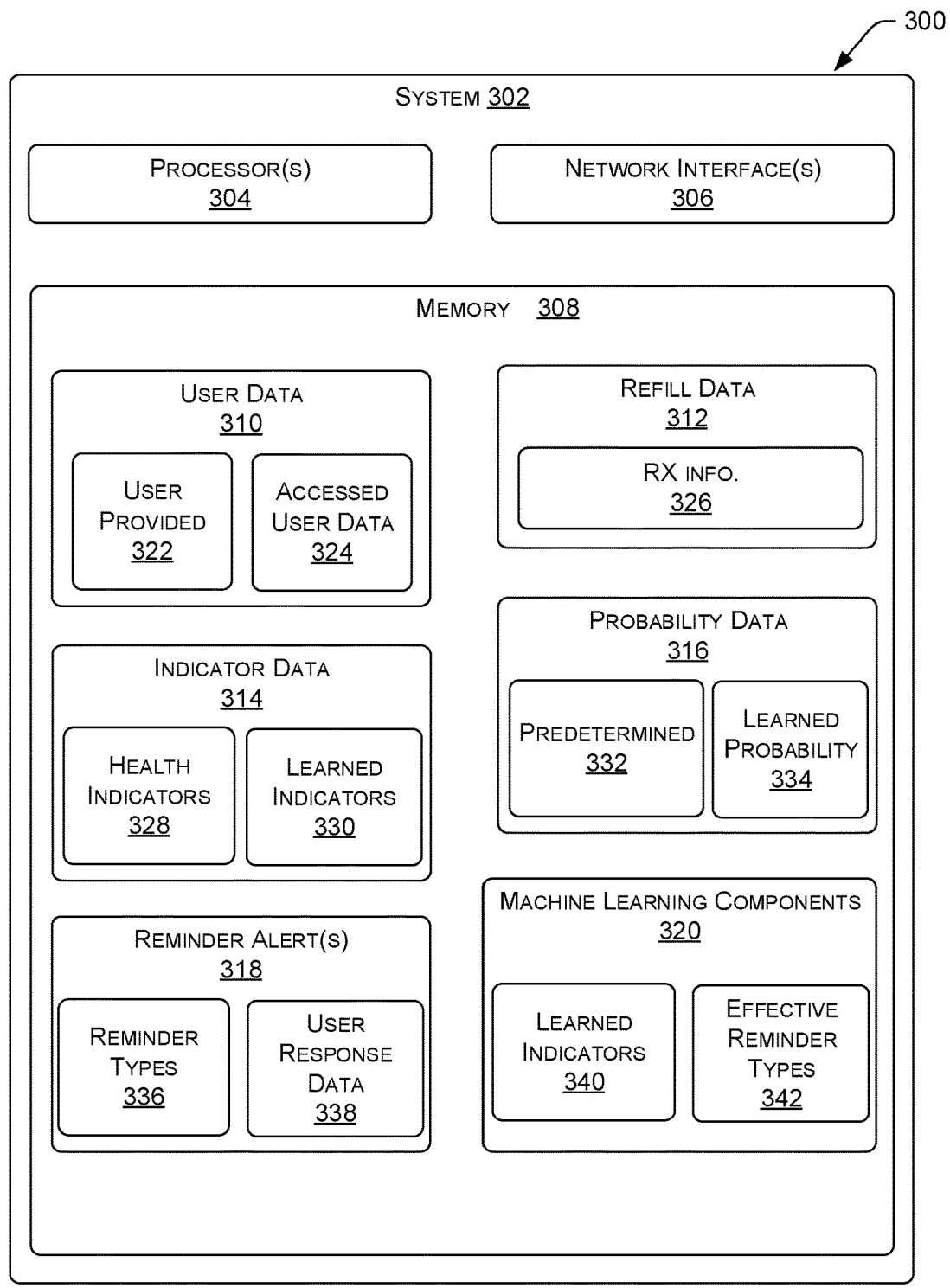
FIG. 3 illustrates a functional block diagram of an example system for prospective medication fillings management.

FIG. 3 illustrates a functional block diagram 300 of an example system 302 for prospective medication fillings management. The system 300 may perform the same or similar functions as the system 102 described in FIG. 1. The system 300 may comprise processor(s) 304 that are operatively connected to an input interface 306 and a memory 308.

The memory 308 may store user data 310, refill data 312, indicator data 314, probability data 316, reminder alert(s) 318, and/or machine learning components 320. In examples, the user data 310 may include both user provided data 310 and accessed user data 324. For example, the user provided data 310 may include personal data provided by one or more users during a setup or onboarding process. For instance, the user provided data 310 may include physical characteristics, relationship status, medical history, etc. In examples, the accessed user data 324 may include user data accessed from a third-party system or database. For example, system 302 may access, via the processor(s) 304, a third-party databased or healthcare system and obtain user information associated with one or more users. The system 302 may store the accessed user data 324 within the user data 310 component of the memory 308 for use.

In examples, the memory 308 may store refill data 312 including prescription information 326 provided to the system 302 and associated with one or more medications prescribed to the one or more users. For example, the prescription information may include dosage(s), administration instruction(s), an amount of refills remaining, refill schedule(s), preferred pharmacy location(s), brand information and/or generic equivalents, etc. associated with the prescribed medication(s). The refill data 312 may be utilized by the system to determine such information as when a user is due for a refill (e.g., that a refill of a medication will occur within a certain time period), and/or where the refilling facility is located.

In embodiments, the memory 308 may store indicator data 314 including health indicators 328 and/or learned indicators 330. The health indicators 328 may include one or more health indicators associated with users that have been provided to the system 302 and/or accessed by the system 302. The health indicators may include, but not be limited to, refill history, medical history, chronic ailments, social indicators, physical characteristics, current living information, demographic information, etc. Alternatively, or in addition to, the indicator data 314 may include learned indicators 330. The learned indicators 330 may include one or more health indicators determined by the machine learning components 320. For example, the machine learning components 320 may utilize the user data 310 and refill data 312 to determine one or more health indicators associated with users.

In other embodiments, the memory 308 may store probability data 316 including predetermined probability data 332 and learned probability data 334. The predetermined probability data 332 and learned probability data 334 may include probability data indicating a threshold over which a user is considered high-risk, or more likely to miss a refill of a medication. For example, the predetermined probability data 332 may include probability thresholds that have been predetermined by the system 302 or pre-programmed into the system 302. The predetermined probability data 332 may be calculated based at least in part on historical data, observations, etc. The learned probability data 334 may be determined utilizing the one or more machine learning components 320. For example, the machine learning components 320 may implement one or more predictive algorithms and/or application programming interfaces (APIs) to calculate the learned probability data 334 based at least in part on the user data 310 and refill data 312.

In embodiments, the memory 308 may store reminder alert(s) 318 including reminder types 336 and user response data 338. For example, the reminder types 336 may include one or more types of reminders available for generation and transmission to a user. Examples may include types device notifications (e.g., text messages, call phones, emails, etc.) and/or content to be included in the reminder such as links to assist a user in scheduling a refill, arranging transportation to a refill facility, prerecorded content or notification features, etc. In addition, the user response data 338 may include data indicating an interaction of the user with the reminder, a lack of interaction with the reminder, and/or the type of interaction (e.g., selections) associated with each reminder and/or each reminder type. For example, the user response data 338 may indicate that the user opened the text message reminder alert, but did not select any links included. In another example, the user response data 338 may indicate that the user did not open the reminder alert at all.

In another embodiment, the memory 308 may store one or more machine learning components 320 including learned indicator data 340 and effective reminder types 342. For example, the machine learning components 320 may implement one or more machine learning algorithms to train one or more indicator model(s), such as indicator model(s) 206 described in Figured 2, to determine one or more health indicators associated with users and, in addition, to identify which of the one or more health indicators, alone or in combination, are associated with users that are more likely to miss a refill, respond to or ignore a refill reminder, and/or the type, content, delivery method, etc. associated with a refill reminder that the user has, or is likely to, respond to.

In addition, the machine learning components 320 may implement one or more machine learning algorithms to determined one or more effective reminder types 342 indicating reminder types that the user has interacted with and/or have caused the user to refill his/her medication(s). For example, the machine learning components 320 may determine, based at least in part on the reminder alert(s) data 318 that a certain reminder type is more effective than others (e.g., elicits a higher user response and/or causes more users to refill their medications). In addition, the machine learning components 320 may determine which reminder type is most effective for a user associated with one or more health indicators. For example, over time, it may be determined that text message notifications cause more users under a certain age to interact with the text message and/or schedule a refill as a result of the text message. The machine learning component(s) 320 may execute any type of supervised learning algorithms (e.g., nearest neighbor, Naïve Bayes, Neural Networks, unsupervised learning algorithms, semi-supervised learning algorithms, reinforcement learning algorithms, and so forth.

As used herein, a processor, such as processor(s) 304, may include multiple processors and/or a processor having multiple cores. Further, the processors may comprise one or more cores of different types. For example, the processors may include application processor units, graphic processing units, and so forth. In one implementation, the processor may comprise a microcontroller and/or a microprocessor. The processor(s) 304 may include a graphics processing unit (GPU), a microprocessor, a digital signal processor or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, at least some of the processor(s) 110 may possess its own local memory, which also may store program components, program data, and/or one or more operating systems.

The memory 308 may include volatile and nonvolatile memory, removable and non-removable media implemented in any method or technology for storage of information, such as computer-readable instructions, data structures, program component, or other data. Such memory 114 includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device. The memory 308 may be implemented as computer-readable storage media ("CRSM"), which may be any available physical media accessible by the processor(s) 110 to execute instructions stored on the memory 308. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other tangible medium which can be used to store the desired information and which can be accessed by the processor(s).

Further, functional components may be stored in the respective memories, or the same functionality may alternatively be implemented in hardware, firmware, application specific integrated circuits, field programmable gate arrays, or as a system on a chip (SoC). In addition, while not illustrated, each respective memory, such as memory 308, discussed herein may include at least one operating system (OS) component that is configured to manage hardware resource devices such as the network interface(s), the I/O devices of the respective apparatuses, and so forth, and provide various services to applications or components executing on the processors. Such OS component may implement a variant of the FreeBSD operating system as promulgated by the FreeBSD Project; other UNIX or UNIX-like variants; a variation of the Linux operating system as promulgated by Linus Torvalds; the FireOS operating system from Amazon.com Inc. of Seattle, Washington, USA; the Windows operating system from Microsoft Corporation of Redmond, Washington, USA; LynxOS as promulgated by Lynx Software Technologies, Inc. of San Jose, California; Operating System Embedded (Enea OSE) as promulgated by ENEA AB of Sweden; and so forth.

The network interface(s) 306 may enable communications between the components and/or devices and/or with one or more other remote systems, as well as other networked devices. Such network interface(s) 306 may include one or more network interface controllers (NICs) or other types of transceiver devices to send and receive communications over a network.

For instance, at least some of the network interface(s) 112 may include a personal area network (PAN) component to enable communications over one or more short-range wireless communication channels. For instance, the PAN component may enable communications compliant with at least one of the following standards IEEE 802.15.4 (ZigBee), IEEE 802.15.1 (Bluetooth), IEEE 802.11 (WiFi), or any other PAN communication protocol. Furthermore, at least some of the network interface(s) 306 may include a wide area network (WAN) component to enable communication over a wide area network.

Figure 4:
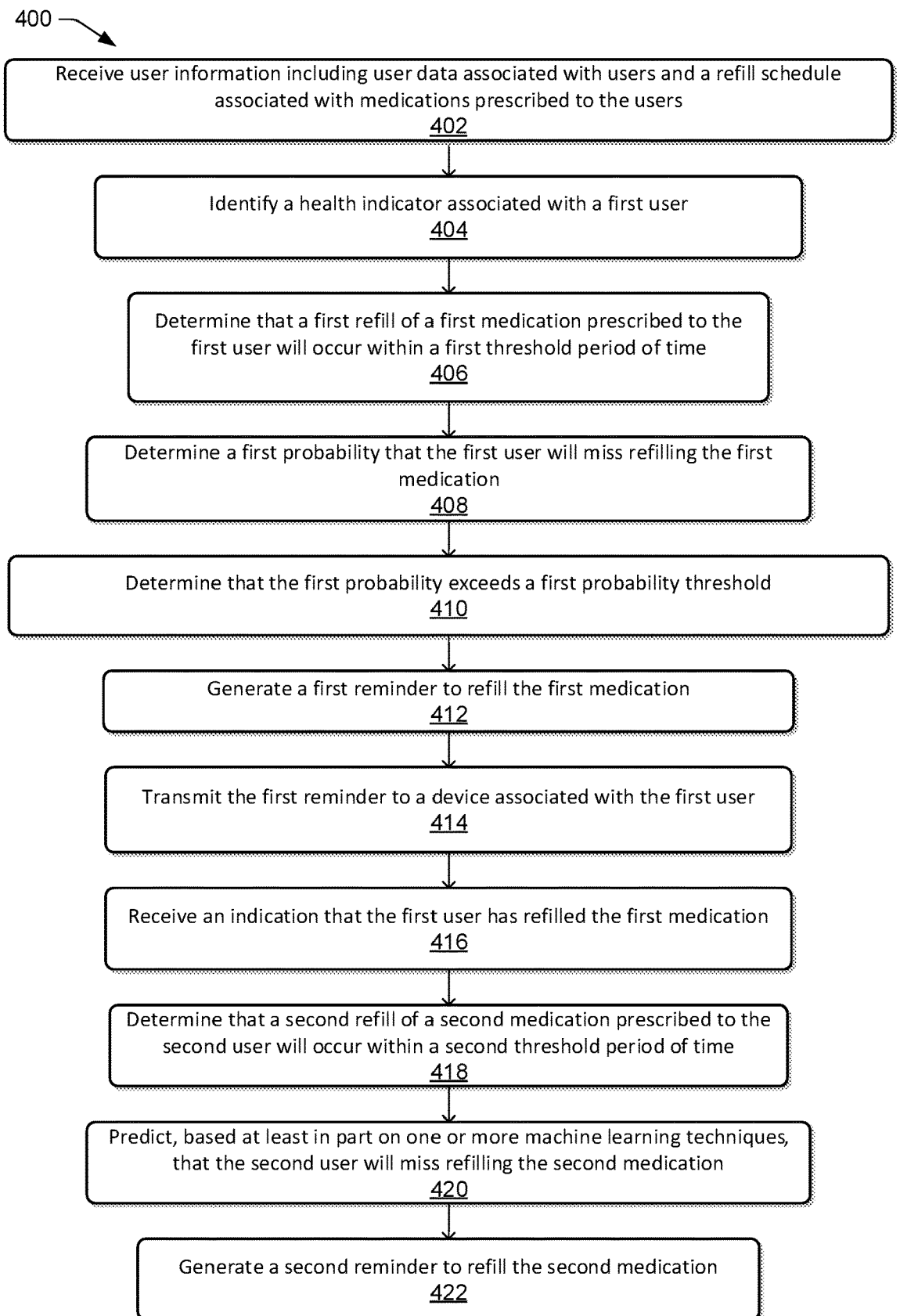
Figure 6:
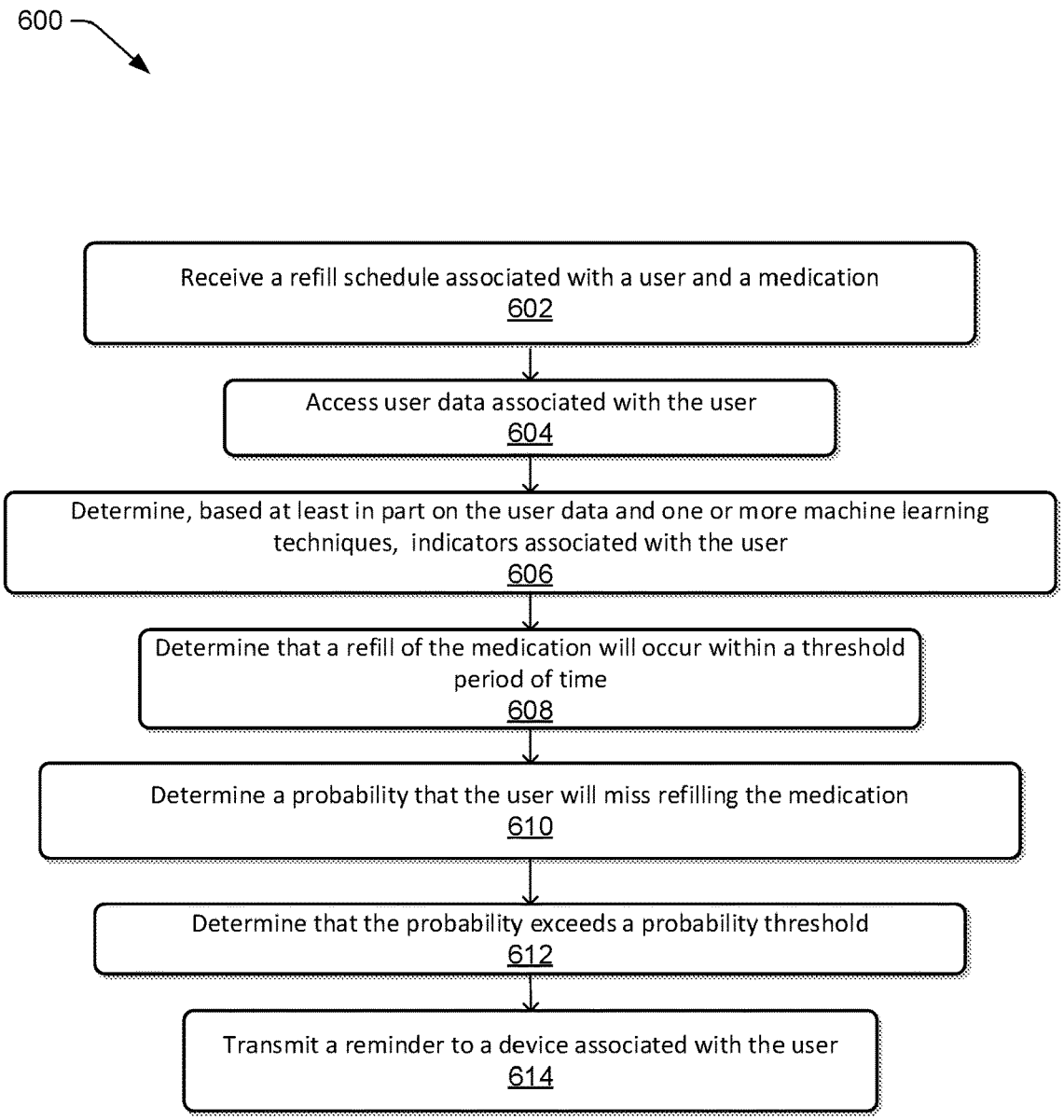

FIGS. 4-6 illustrate various flow diagrams of example processes for prospective medication fillings management. The processes described herein are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, architectures and systems described in the examples herein, such as, for example those described with respect to FIGS. 1-3, although the processes may be implemented in a wide variety of other environments, architectures, and systems.

FIG. 4 illustrates a flow diagram of an example process 400 for medication fillings management. The order in which the operations or steps are described is not intended to be construed as a limitation, and any number of the described operations may be combined in any order and/or in parallel to implement process 400.

At block 402, the process 400 may include receiving user information including user data associated with users and a refill schedule associated with medications prescribed to the users. For example, the systems for medication fillings management described herein may receive user information including user data and a refill schedule. The user data may include data associated with the users such as personal data, demographic data, health data, physical characteristic data, prescription medication data, and/or social data. The refill schedule may include dates when the user is due for a refill and/or medication information such as the brand, dosage, refills remaining, preferred pharmacy, accepted generics, etc.

At block 404, the process 400 may include identifying a health indicator associated with a first user. For example, the system may access and/or analyze the user data and/or refill data to determine health indicators associated with the first user such as a refill history, medical conditions, physical characteristics, social indicators, etc. Alternatively, or in addition to, the system may utilize one or more machine learning techniques to determine the health indicator, as described herein.

At block 406, the process 400 may include determining that a refill of a first medication will occur within a first threshold period of time. For example, the system may analyze the refill schedule associated with the user and the medication to determine that the user is due for a refill within a certain timeframe/period of time.

At block 408, the process 400 may include determining a first probability that the first user will miss refilling the first medication. For example, the system may analyze the user data and/or health indicators, such as the refill history, to determine that the user will miss his/her refill. For instance, the system may analyze the refill history of the user to determine that the user has missed 30% of his/her past refills and, therefore, determine a probability that the user will miss the upcoming refill of the medication. Alternatively, or in addition to, the system may utilize the one or more machine learning techniques to determine the first probability, as described herein.

At block 410, the process 400 may include determining that the first probability exceeds a first probability threshold. For example, the system may compare the first probability to a threshold to determine if the first probability exceeds the probability threshold. In examples, the first probability threshold may be predetermined or pre-programmed into the system. In other examples, the first probability threshold may be determined via one or more machine learning techniques, as described herein.

At block 412, the process 400 may include generating a first reminder to refill the first medication. For example, in response to determining that the first probability exceeds the probability threshold, the system may determine that the user is high-risk, meaning he/she is likely to miss the refill, and therefore needs a reminder. As such, the system may generate a reminder to refill the medication. The reminder may include a variety of content, such as links to schedule the refill or to choose a refill facility, as well as a variety of delivery formats, such as text, email, or phone call.

At block 414, the process 400 may include transmitting the first reminder to a device associated with the first user. For example, the system may transmit the first reminder to a user device such as a smart phone, computer, tablet, etc.

At block 416, the process 400 may include receiving an indication that the first user has refilled the first medication. For example, the system may receive an indication that the first user has refilled the first medication directly from the user or from the refill facility. In examples, the indication may also indicate that the user has interacted with the reminder and/or the type of interaction. The indication may help the system determine whether the refill was aided, or the result of, the reminder and/or whether the reminder was an effective, in both form of communication and content, in achieving user interaction.

At block 418, the process 400 may include determining that a refill of a second medication will occur within a second threshold period of time. For example, the system may access the user data and/or refill schedules and determine that a second user is due for a medication refill.

At block 420, the process 400 may include predicting, based at least in part on one or more machine learning techniques, that the second user will miss refilling the second medication. For example, the system may implement one or more machine learning techniques, as described herein, that may determine, over time, health indicators, individually or in combination, that are associated with users likely to miss a refill. As such, when another user is due for a refill, the system may be able to determine one or more health indicators associated with the user and determine if the one or more health indicators are associated with those determined by the system to be associated with high-risk users. If the indicators are associated (e.g., if indicators of the user and indicators of a high-risk user have an exact match and/or partial match, if combinations of indicators of a high-risk user and indicators of the user have a full and/or partial overlap, if indicators of the user match with various combinations of indicators deemed to be high-risk, etc.), the system may predict that the second user will also miss refilling his/her medication.

At block 422, the process 400 may include generating a second reminder to refill the second medication. For example, the system may generate a second reminder for transmission to the second user to remind him/her to refill their medication in a timely manner.

FIG. 5 illustrates a flow diagram of another example process 500 for medication fillings management. The order in which the operations or steps are described is not intended to be construed as a limitation, and any number of the described operations may be combined in any order and/or in parallel to implement process 500.

At block 502, the process 500 may include receiving data from additional users including reminders to refill reminders sent to devices associated with the additional users and indications that the additional users have refilled the medications. For example, the system may receive data that includes refill reminder alert(s) that have been sent to the additional users in response to determining that the user(s) are high-risk, or likely to miss a refill, by one or more of the techniques described herein such as machine learning, evaluating health indicators associated with the user(s), etc. Additionally, the system may receive indications that users have refilled the medications. The indications may come directly from the user, user device, and/or the refill facility. In examples, the indications may also indicate which users have interacted with the reminder, the type of reminder, and/or the type of interaction. These indications may help the system determine whether the refills were aided by, or are the result of, the reminders and/or whether the reminders were effective, in both form of communication and content, and in achieving general user interaction.

At block 504, the process 500 may include determining, based on machine learning techniques, combinations of indicators that are associated with probabilities exceeding the first probability threshold, the probabilities indicating that the additional users will miss refills. For example, the one or more machine learning techniques, over time, may determine the certain combinations of indicators are associated with users who are more likely to miss a refill, as described herein. As the system analyzes data associated with more users, the system may be able to more accurately determine the indicators associated with the most high-risk users.

At block 506, the process 500 may include determining that a refill of a medication will occur within a threshold period of time. For example, the system may access the user data and/or refill schedules and determine that a user is due for a medication refill within a certain time frame. Alternatively, or in addition to, the system may receive a notification that the user is due for a refill from a medical facility, the refill facility, etc.

At block 508, the process 500 may include predicting, based at least in part on the combinations of indicators and machine learning techniques, that the user will miss refilling the medication. For example, the system may determine one or more indicators associated with the user and may compare the one or more indicators to high-risk combinations determined at block 504. If there is an association, the system may determine that the user is at risk for missing a medication refill. For example, the association may compromise an overlap of combinations of indicators, a full or partial matching of indicators, etc.

At block 510, the process 500 may include generating a reminder to refill the medication. For example, the system may generate a reminder for transmission to the user to remind him/her to refill their medication in a timely manner.

FIG. 6 illustrates a flow diagram of another example process 600 for medication fillings management. The order in which the operations or steps are described is not intended to be construed as a limitation, and any number of the described operations may be combined in any order and/or in parallel to implement process 600.

At block 602, the process 600 may include receiving a refill schedule associated with a user and a medication. For example, the systems for medication fillings management described herein may receive a refill schedule. The refill schedule may include dates when the user is due for a refill and/or medication information such as the brand, dosage, remaining refills, preferred refill method, accepted generics, etc.

At block 604, the process 600 may include accessing user data associated with the user. For example, the system may access user data associated with the user either from a local user data database and/or from a third-party database or system having user data associated with the user.

At block 606, the process 600 may include determining, based at least in part on the user data and one or more machine learning techniques, indicators associated with the user. For example, the system may access and/or analyze the user data and/or refill schedule to determine one or more health indicators associated with the user. Alternatively, or in addition to, the system may utilize one or more machine learning techniques to determine the one or more health indicators, as described herein. For example, the indicator model(s) 206 may be trained to determine one or more health indicators associated with the user, such as an indicator indicating a refill history associated with the user based on historical refill data.

At block 608, the process 600 may include determining that a refill of the medication will occur within a threshold period of time. For example, the system may analyze the refill schedule to determine that the user is dur for a refill.

At block 610, the process 600 may include determining a probability that the user will miss refilling the medication. For example, the system may analyze the user data and/or health indicators to determine that the user will miss his/her refill. For instance, the system may analyze a social health indicator of the user to determine that the user does not have a motor vehicle and lives very distance from the refill facility and, therefore, determine a probability that the user will miss the upcoming refill of the medication. Alternatively, or in addition to, the system may utilize the one or more machine learning techniques to determine the probability, as described herein.

At block 612, the process 600 may include determining that the probability exceeds a probability threshold. For example, the system may compare the probability to a threshold to determine if the probability exceeds the probability threshold. In examples, the first probability threshold may be predetermined or pre-programmed into the system. In other examples, the first probability threshold may be determined via one or more machine learning techniques, as described herein.

At block 614, the process 600 may include transmitting a reminder to a device associated with the user. For example, the system may transmit the first reminder to a user device such as a smart phone, computer, tablet, etc.

At block 616, the process 600 may include receiving an indication that the first user has refilled the first medication. For example, the system may receive an indication that the user has placed the request for the refill or picked up the refill from the refill facility. In examples, the indication may also indicate that the user has interacted with the reminder and/or the type of interaction to help determine an effectiveness associated with the reminder.

At block 618, the process 600 may include determining that a second user is due for a refill of a second medication. For example, the system may access the user data and/or refill schedules and determine that a second user is due for a medication refill.

At block 620, the process 600 may include predicting, based at least in part on one or more machine learning techniques, that the second user will miss refilling the second medication. For example, the system may implement one or more machine learning techniques, as described herein, that may determine, over time, health indicators, individually or in combination, that are associated with users likely to miss a refill. As such, when another user is due for a refill, the system may be able to determine one or more health indicators associated with the user and determine if the one or more health indicators are associated with those determined by the system to be associated with high-risk users. If the indicators are associated, the system may predict that the second user will also miss refilling his/her medication.

At block 622, the process 600 may include generating a second reminder to refill the second medication. For example, the system may generate a second reminder for transmission to the second user to remind him/her to refill their medication prior to the missed refill.

While the foregoing invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A system comprising:
   one or more processors; and
   computer-readable media storing first computer-executable instructions that, when executed by the one or more processors, cause the one or more processors to perform operations comprising:
   receiving user information including (1) user data associated with users, (2) first user input data indicating prior interactions with the system, (3) a refill schedule associated with medications prescribed to the users, and (4) a refill history associated with medications prescribed to the users;
   identifying, based at least in part on the user data, a health indicator associated with a first user of the users, the health indicator including at least one of refill history data, medical history data, social data, or prescription data;
   determining, based at least in part on the refill schedule and the first user input data, that a first refill of a first medication prescribed to the first user will occur within a first threshold period of time;

determining, based at least in part on the health indicator, a first probability that the first user will miss refilling the first medication, the first probability associated with a combination of indicators that the first user will miss refilling the first medication;

determining that the first probability exceeds a first probability threshold;

generating a first machine learning model configured to determine a type of reminder;

training the first machine learning model based at least in part on previous interaction data associated with various reminder types such that a first trained machine learning model is generated;

determining, utilizing the first trained machine learning model, the type of reminder to send, wherein the first trained machine learning model utilizes, as input, (1) the health indicator, (2) the refill schedule, (3) the refill history, (4) the first user input data, (5) previous interaction data of the first user with reminder types, (6) computing devices associated with the first user, and (7) software technology associated with the first user;

generating, based at least in part on the determining that the first probability exceeds the first probability threshold, a first reminder to refill the first medication, the first reminder formatted as the type of reminder, wherein generating the first reminder includes generating an interactive link as at least a portion of the first reminder, the interactive link configured to, when selected by the first user:

display a user interface with a list of selectable actions associated with the first reminder, the selectable actions including scheduling a refill, having the medication delivered to the user, arranging transportation of the user to a location associated with the medication, and preparing the medication for an in-person pickup; and adaptively perform at least one of the selectable actions based at least in part on receiving second user input data indicating selection of the at least one of the selectable actions;

transmitting the first reminder to a device associated with the first user, the first reminder causing an application associated with the device to initiate and cause the user interface to be displayed, the user interface configured to present a visual representation of the first reminder with the interactive link in response to receiving the first reminder at the device;

receiving the second user input data;

generating a second machine learning model configured to predict whether medication fills will be missed;

generating a training dataset corresponding to the health indicator, the first probability, the first reminder, and the second user input data;

training the second machine learning model utilizing at least the training dataset such that a second trained machine learning model is generated by identifying relationships between the health indicator, the first probability, first reminder, and the second user input data;

determining, based at least in part on the refill history, that a second refill of a second medication prescribed to a second user will occur within a second threshold period of time;

generating input data representing health indicators associated with the second user, the input data formatted for input to the second trained machine learning model;

generating, utilizing the second trained machine learning model and the input data, results data indicating the second user will miss refilling the second medication; and generating, based at least in part on the results data, a second reminder to refill the second medication.

2. The system of claim 1, wherein the social data includes data associated with at least one of a marital status, a housing status, or a caregiver status.

3. The system of claim 1, wherein the health indicator comprises first health indicators, the operations further comprising at least one of:

determining, based at least in part on machine learning techniques, that a first combination of the first health indicators is associated with the first probability exceeding the first probability threshold; or determining, based at least in part on the machine learning techniques, that a second combination of the first health indicators is associated with the first probability being below the first probability threshold.

4. The system of claim 3, the operations further comprising:

identifying, based at least in part on the user data, the second user input data, second health indicators associated with the second user;

comparing the second indicators to the first combination of the first health indicators; and determining an association between the second indicators and the first combination of the first health indicators.

5. The system of claim 1, the operations further comprising:

receiving data from additional users, the data including reminders to refill medications sent to devices associated with the additional users and indications that the additional users have refilled the medications;

determining, based at least in part on machine learning techniques, combinations of indicators that are associated with probabilities exceeding the first probability threshold, the probabilities indicating that the additional users will miss refills;

determining, based at least in part on the refill history, that a third refill of a third medication prescribed to a third user will occur within a third threshold period of time;

predicting, based at least in part on the combinations of indicators and the machine learning techniques, that the third user will miss refilling the third medication; and generating, based at least in part on the prediction that the third user will miss refilling the third medication, a third reminder to refill the third medication.

6. The system of claim 5, the operations further comprising:

identifying, based at least in part on the user data, third health indicators associated with the third user;

comparing the third health indicators to the combinations of the indicators; and determining an association between the third health indicators and a combination of the combinations.

7. The system of claim 5, wherein generating the third reminder to refill the third medication includes generating the type of reminder associated with the combination.

8. The system of claim 1, the operations further comprising:
   determining a device type of the device; and
   wherein generating the reminder is based at least in part on the device type.

9. A computer-implemented method comprising:
   generating a first machine learning model configured to predict whether medication fills will be missed;
   generating a training dataset corresponding to multiple health indicators associated with users and first user input data associated with users that reminders sent to the users led to successful medication fills;
   training the first machine learning model utilizing at least the training dataset such that a first trained machine learning model is generated by identifying relationships between the multiple health indicators and the first user input data that reminders sent to the users led to successful medication fills;
   receiving health indicators associated with a user, the user prescribed a medication;
   generating input data representing the health indicators associated with the user and the first user input data associated with the user, the input data formatted for input to the first trained machine learning model;
   generating, utilizing the first trained machine learning model and the input data, results data indicating a probability that the user will miss refilling the medication exceeds a threshold probability, the probability associated with a combination of indicators that the user will miss refilling the first medication;
   receiving a notification that a refill of the medication will occur within a threshold period of time;
   generating a second machine learning model configured to determine a type of reminder to send;
   training the second machine learning model based at least in part on previous interaction data associated with various reminder types such that a second trained machine learning model is generated;
   determining, utilizing the second trained machine learning model, the type of reminder associated with the combination using (1) the health indicators, (2) previous interaction data of the user with reminder types, (3) second user input data associated with the user, (4) computing devices associated with the user, and (5) software technology associated with the user; and
   based at least in part on receiving the notification and the results data, transmitting a reminder to a device associated with the user, wherein the reminder includes an interactive link as at least a portion of the reminder, the interactive link configured to, when selected by the user:
      display a user interface with a list of selectable actions associated with the first reminder, the selectable actions including scheduling a refill, having the medication delivered to the user, arranging transportation of the user to a location associated with the medication, and preparing the medication for an in-person pickup; and
      adaptively perform at least one of the selectable actions based at least in part on receiving the second user input data indicating selection of the at least one of the selectable actions, the reminder causing an application associated with the device to initiate and cause a user interface to be displayed, the user interface configured to present a visual representation of the reminder including the interactive link in response to receiving the reminder at the device, the reminder being of the type of reminder associated with the combination.

10. The computer-implemented method of claim 9, the method further comprising:
   determining, based at least in part on machine learning techniques, that a combination of the health indicators and historical user input data is associated with the probability exceeding the probability threshold.

11. The computer-implemented method of claim 10, wherein the user comprises a first user, the health indicators comprise first health indicators, the medication comprises a first medication, and the threshold period of time comprises a first threshold period of time, the method further comprising:
   receiving second health indicators associated with a second user, the second user prescribed a second medication;
   receiving a second notification that a second refill of the second medication will occur within a second threshold period of time;
   predicting, utilizing the first trained machine learning model, that the second user will miss refilling the second medication; and
   generating, based at least in part on the prediction, a second reminder to refill the second medication.

12. The computer-implemented method of claim 11, wherein predicting that the second user will miss refilling the second medication comprises:
   comparing the second health indicators associated with the second user to the combination of the health indicators; and
   determining an association between the second health indicators and the combination.

13. The computer-implemented method of claim 9, further comprising:
   determining a device type of the device; and
   wherein generating the reminder is based at least in part on the device type.

14. A method comprising:
   generating a first machine learning model configured to predict whether medication fills will be missed;
   generating a training dataset corresponding to health-related data associated with users and first user input data indicating prior interactions with a medication-related system that led to successful medication fills or refills;
   training the first machine learning model utilizing at least the training dataset such that a first trained machine learning model is generated by identifying relationships between the health-related data associated with users, the first user input data, and the reminders sent to the users led to successful medication fills;
   receiving a refill schedule associated with a user and a medication;
   accessing user data associated with the user;
   determining, based at least in part on the user data, indicators associated with the user;
   determining, based at least in part on the refill history, that a refill of the medication will occur within a threshold period of time;
   generating input data representing the indicators associated with the user, the input data formatted for input to the first trained machine learning model;
   generating, utilizing the first trained machine learning model and the input data, results data indicating a probability that the user will miss refilling the medication satisfies a probability threshold, the probability associated with a combination of indicators that the user will miss refilling the first medication;

generating a second machine learning model configured to determine a reminder type to send;

training the second machine learning model based at least in part on previous interaction data associated with various reminder types such that a second trained machine learning model is generated;

determining, utilizing the second trained machine learning model, the type of reminder associated with the combination using (1) the indicators associated with the user, (2) the refill schedule, (3) the refill history, (4) the second user input data, (5) previous interaction data of the user with reminder types, (6) computing devices associated with the user, and (7) software technology associated with the user; and transmitting, based at least in part on the results data, a reminder to a device associated with the user, wherein the reminder includes an interactive link as at least a portion of the reminder, the interactive link configured to, when selected by the first user:

display a user interface with a list of selectable actions associated with the first reminder, the selectable actions including scheduling a refill, having the medication delivered to the user, arranging transportation of the user to a location associated with the medication, and preparing the medication for an in-person pickup; and adaptively perform at least one of the selectable actions based at least in part on receiving third user input data indicating selection of the at least one of the selectable actions, the reminder causing an application associated with the device to initiate and cause the user interface to be displayed, the user interface configured to present a visual representation of the reminder in response to receiving the reminder at the device, the reminder formatted as the type of reminder associated with the combination.

15. The method of claim 14, wherein the indicators include at least one of refill history data, medical history data, social data, or prescription data.

16. The method of claim 14, the method further comprising determining that a combination of the indicators is associated with the probability exceeding the probability threshold.

17. The method of claim 14, wherein the user is a first user, the medication is a first medication, the threshold period of time is a first threshold period of time, and the reminder is a first reminder, the method further comprising:

accessing data from additional users, the data including reminders to refill medications sent to devices associated with the additional users and indications that the additional users have refilled the medications;

determining combinations of indicators that are associated with probabilities exceeding the probability threshold, the probabilities indicating that the additional users will miss refills;

determining, based at least in part on the data, that a refill of a second medication prescribed to the second user will occur within a second threshold period of time;

predicting, based at least in part on the first trained machine learning model, that the second user will miss refilling the second medication; and generating, based at least in part on the prediction that the second user will miss refilling the second medication, a second reminder to refill the second medication.

18. The method of claim 17, wherein the indicators are first indicators and the predicting that the second user will miss refilling the second medication comprises:

accessing second user data associated with the second user;

determining, based at least in part on the second user data, second indicators associated with the second user;

comparing the second indicators to the combinations of indicators; and determining an association between the second health indicators and a combination of the combinations.

19. The method of claim 17, the method further comprising determining, based at least in part on the indications received, that the type of reminder of the reminders is associated with a threshold number of the indications.

20. The method of claim 14, further comprising:
  determining a device type of the device; and
  wherein generating the reminder is based at least in part on the device type.

* * * * *